(12) United States Patent
Daly et al.

(10) Patent No.: US 10,219,556 B2
(45) Date of Patent: Mar. 5, 2019

(54) ACTIVELY CONTROLLED PERFORMANCE CLOTHING

(71) Applicant: International Business Machines Corporation, Armonk, NY (US)

(72) Inventors: David M Daly, Yorktown Heights, NY (US); David Joel Edelsohn, White Plains, NY (US); Kaoutar El Maghraoui, Yorktown Heights, NY (US); Jose Eduardo Moreira, Irvington, NY (US); Priya A Nagpurkar, Ossining, NY (US); Jessica Hui-Chun Tseng, Fremont, CA (US)

(73) Assignee: International Business Machines Corporation, Armonk, NY (US)

( * ) Notice: Subject to any disclaimer, the term of this patent is extended or adjusted under 35 U.S.C. 154(b) by 345 days.

(21) Appl. No.: 14/966,540

(22) Filed: Dec. 11, 2015

(65) Prior Publication Data

US 2017/0164664 A1    Jun. 15, 2017

(51) Int. Cl.
| | | |
|---|---|---|
| A41D 13/00 | (2006.01) | |
| A41D 31/00 | (2006.01) | |
| A41D 13/002 | (2006.01) | |
| A61B 5/00 | (2006.01) | |
| A61B 5/0205 | (2006.01) | |

(Continued)

(52) U.S. Cl.
CPC ....... *A41D 13/002* (2013.01); *A41D 13/0015* (2013.01); *A61B 5/6804* (2013.01); *A61B 5/024* (2013.01); *A61B 5/02055* (2013.01); *A61B 5/1112* (2013.01); *A61B 2560/0242* (2013.01); *A61B 2560/0462* (2013.01); *A61B 2562/029* (2013.01); *A61B 2562/0247* (2013.01); *A61B 2562/0271* (2013.01); *A61B 2562/12* (2013.01)

(58) Field of Classification Search
CPC .......................... A41D 13/002; A41D 13/0015
USPC ...................................................... 2/69, 243.1
See application file for complete search history.

(56) References Cited

U.S. PATENT DOCUMENTS 3,999,039 A * 12/1976 Groth ...................... C23C 14/26
                                                              392/389
4,404,460 A *  9/1983 Kerr .................... A41D 13/0051
                                                                 2/69

(Continued)

FOREIGN PATENT DOCUMENTS

GB        002244637 A     12/1991

OTHER PUBLICATIONS

S. Mondal "Phase change materials for smart textiles", 2007 Elsevier.

(Continued)

*Primary Examiner* — Timothy K Trieu
(74) *Attorney, Agent, or Firm* — Derek S. Jennings; Patent Mining Works, LLC

(57) ABSTRACT

A method includes embedding clothing with at least one sensor and at least one control unit; a power unit powering on the at least one sensor and the at least one control unit; the at least one sensor monitoring a sensed condition; the at least one control unit conducting a heat prediction based on the sensed condition; and the at least one control unit controlling threads within the clothing based on the heat prediction to actively adjust properties of the clothing.

5 Claims, 4 Drawing Sheets

(51) Int. Cl.
    *A61B 5/024*    (2006.01)
    *A61B 5/11*    (2006.01)

(56) References Cited

U.S. PATENT DOCUMENTS

| | | | |
|---|---|---|---|
| 5,148,002 A * | 9/1992 | Kuo | H01Q 1/273 |
| | | | 219/211 |
| 7,186,957 B2 | 3/2007 | Martin | |
| 7,721,349 B1 | 5/2010 | Strauss | |
| 7,787,726 B2 | 8/2010 | Ten Eyck et al. | |
| 7,891,019 B2 | 2/2011 | Goldfine | |
| 2001/0002669 A1* | 6/2001 | Kochman | A41D 13/0051 |
| | | | 219/545 |
| 2002/0164473 A1 | 11/2002 | Buckley | |
| 2012/0246795 A1* | 10/2012 | Scheffler | A41D 1/002 |
| | | | 2/69 |
| 2013/0205462 A1 | 8/2013 | Kitaura et al. | |
| 2014/0097944 A1 | 4/2014 | Fastert et al. | |

OTHER PUBLICATIONS

J. Rantanen et al., "Smart Clothing for the Arctic Environment", 2000 IEEE.

* cited by examiner

ACTIVELY CONTROLLED PERFORMANCE CLOTHING

BACKGROUND

The present invention relates to controlling performance clothing, and more specifically, to using sensors and control units to actively adjust properties of the performance clothing.

Performance clothing is a major market. Technical clothing are designed to be layered. If it is too hot for a wearer layers can be removed. If it is too cold layers can be added.

Performance clothing is used by people when performing some physical activity outdoors. Whether the activity is for work, sports or leisure, performance clothing is expected to keep the person wearing it thermally comfortable (not too hot, not too cold) through a spectrum of weather (rain, snow, sun, wind, hot, cold) and body (sweating, shivering, running, idle) conditions.

SUMMARY

According to one aspect of the present invention, a method includes embedding clothing with at least one sensor and at least one control unit; a power unit powering on the at least one sensor and the at least one control unit; the at least one sensor monitoring a sensed condition; the at least one control unit conducting a heat prediction based on the sensed condition; and the at least one control unit controlling threads within the clothing based on the heat prediction to actively adjust properties of the clothing.

According to another aspect of the present invention, a system Includes one or more processors, one or more computer-readable memories and one or more computer-readable, tangible storage devices; a power module operatively coupled to at least one of the one or more storage devices for execution by at least one of the one or more processors via at least one of the one or more memories, configured to power embedded elements in clothing; the embedded elements operatively coupled to at least one of the one or more storage devices for execution by at least one of the one or more processors via at least one of the one or more memories, configured to monitor a sensed condition; the embedded elements operatively coupled to at least one of the one or more storage devices for execution by at least one of the one or more processors via at least one of the one or more memories, further configured to conduct a heat prediction based on the sensed condition; and the embedded elements operatively coupled to at least one of the one or more storage devices for execution by at least one of the one or more processors via at least one of the one or more memories, still further configured to control threads within the clothing based on the heat prediction to actively adjust properties of the clothing.

According to yet another aspect of the present invention, a computer includes: one or more computer-readable storage medium, wherein the computer readable storage medium is not a transitory signal per se; program instructions, stored on at least one of the one or more storage medium, to power embedded elements in clothing; program instructions, stored on at least one of the one or more storage medium, to monitor a sensed condition; program instructions, stored on at least one of the one or more storage medium, to conduct a heat prediction based on the sensed condition; and program instructions, stored on at least one of the one or more storage medium, to control threads within the clothing based on the heat prediction to actively adjust properties of the clothing.

BRIEF DESCRIPTION OF THE OF THE DRAWINGS

DETAILED DESCRIPTION

Figure 1:
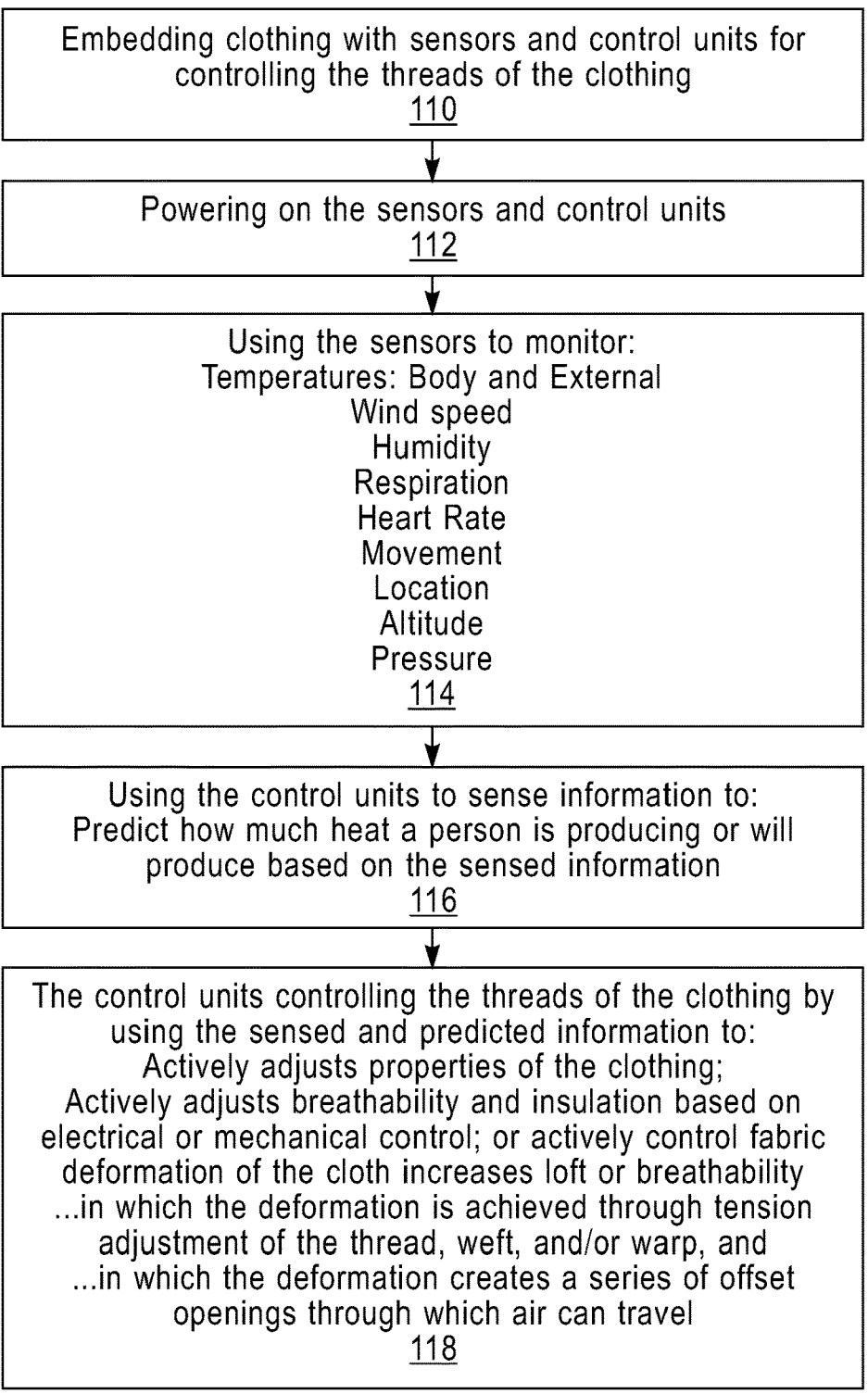
FIG. 1 shows a flowchart according to an embodiment of the present invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting. As will be appreciated by one skilled in the art, aspects of the present invention may be embodied as a system, method or computer program product.

The use of active monitoring and control provides for better control for technical clothing. Now referring to FIG. 1, shown is a process according to an embodiment of the present invention. The process starts by embedding clothing with sensors and control units for controlling the threads of the clothing (110). The embedded clothing containing the sensors and control units are powered up (112). Once the sensors are powered up they monitor a plurality of conditions (114) including: temperatures (wearer's body and external), wind speed, humidity, respiration, heart rate, movement, location, altitude, pressure, etc. The process continues by using the information from the embedded sensors to have the control units predict how much heat a wearer is producing, or will produce, based on the sensed information (116). The process further continues by having the control units control the threads of the clothing by using the sensed and predicted information (118). The process actively adjusts properties of the clothing by:

Actively adjusts breathability and insulation based on electrical or mechanical control; or
Actively control fabric deformation of the cloth increases loft or breathability:
  the deformation is achieved through tension adjustment of the thread, weft, and/or warp, and
  in which the deformation creates a series of offset openings through which air can travel.

Figure 2A:
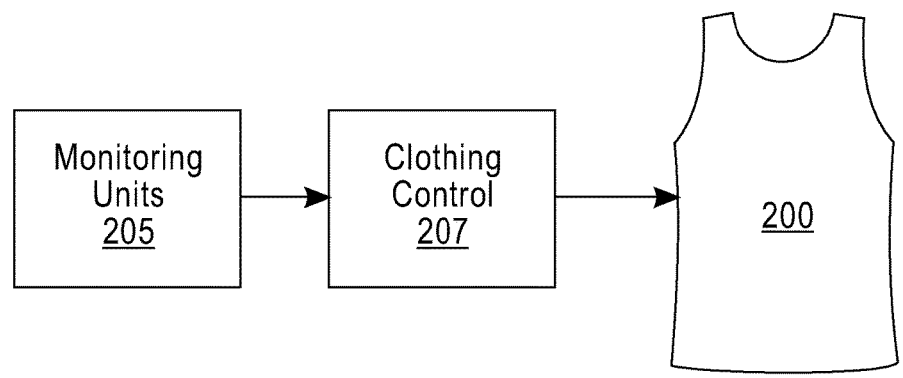
FIGS. 2A-2D show exemplary implementations according to embodiments of the present invention.
Figures 2B, 2C:
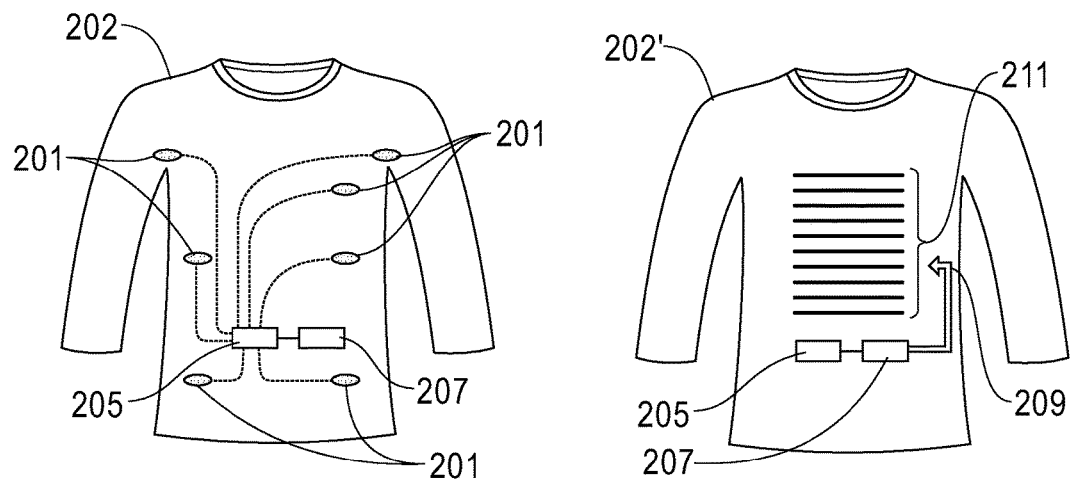
Figure 2D:
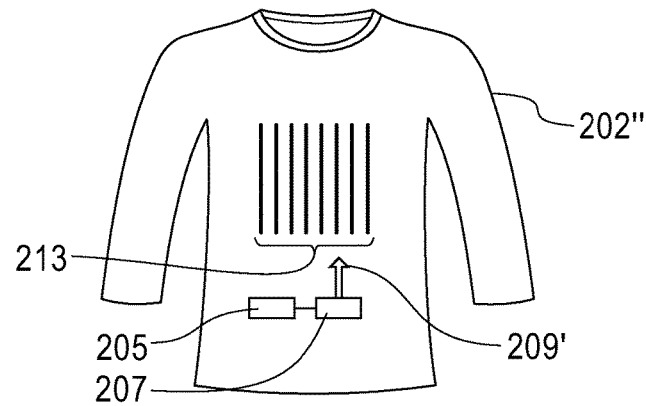

Referring to FIGS. 2A-2D, exemplary implementations according to embodiments of the present invention are depicted. A first embodiment of the present invention includes a monitoring unit 205 to sense a plurality of conditions, as previously mentioned with regard the above process. The monitoring unit 205 uses the sensed information to make a prediction as to how much heat a wearer is producing, or will produce. A control unit 207 receives a prediction signal from the monitoring unit 205 and uses this signal to control the threads of clothing 200, by either allowing for increased or decreased airflow. By way of another exemplary implementation, shown in FIG. 2B are the placement of sensors 201 within a clothing 202. A monitoring unit 205 receives the raw sensor information from the sensors 201. The monitoring unit 205 uses the combined sensed information to produce a prediction control signal. A control unit 207 receives a prediction signal from the monitoring unit 205 and uses this signal to control the threads of clothing 202, by either allowing for increased or decreased airflow. FIG. 2C shows a further implementation of the embodiment according to the present invention. Clothing 202' has embedded therein the monitoring unit 205 and the control unit 207. The control unit produces a signal 209 to actively adjust the treads 211 of the clothing 202'. The controlling threads 211 are shown in the horizontal plane of the clothing 202'. FIG. 2D shows yet another implementation of the embodiment according to the present invention. Clothing 202" has embedded therein the monitoring unit 205 and the control unit 207. The control unit produces a signal 209' to actively adjust the treads 213 of the clothing 202". The controlling threads 213 are shown in the vertical plane of the clothing 202". Additional details of how the controlling threads and how they are controlled will be described hereafter.

Figure 3:
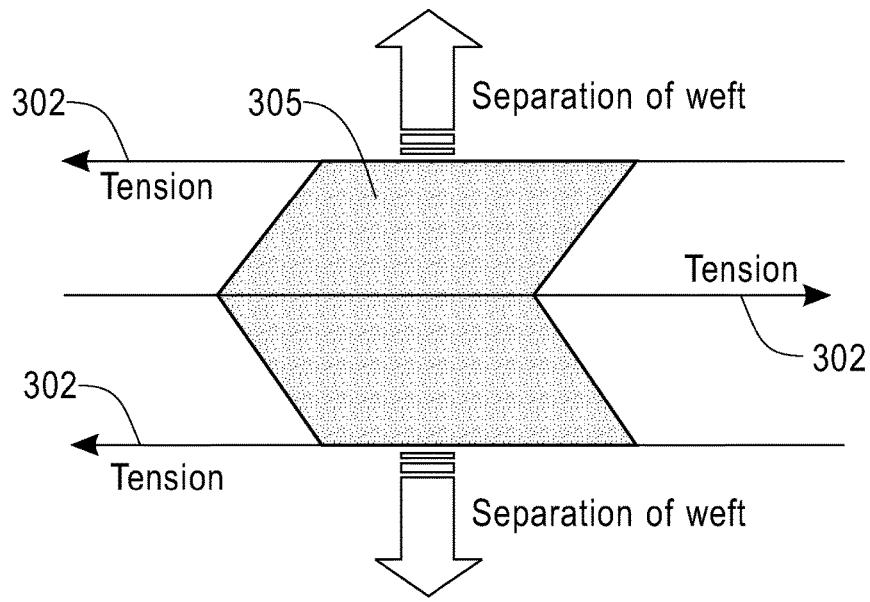
FIG. 3 shows yet exemplary implementation according to an embodiment of the present invention.

Referring to FIG. 3, shown is active plane control of threads according to an embodiment of the present invention. Plane area 305 of the clothing includes a plurality of threads having tension points 302. When the tension points 302 are pulled in opposite directions, as shown, causes a separation of weft. The separation of weft opens the ventilation between two planes by separating the planes with checkerboard patterns of fabric squares.

Figure 4:
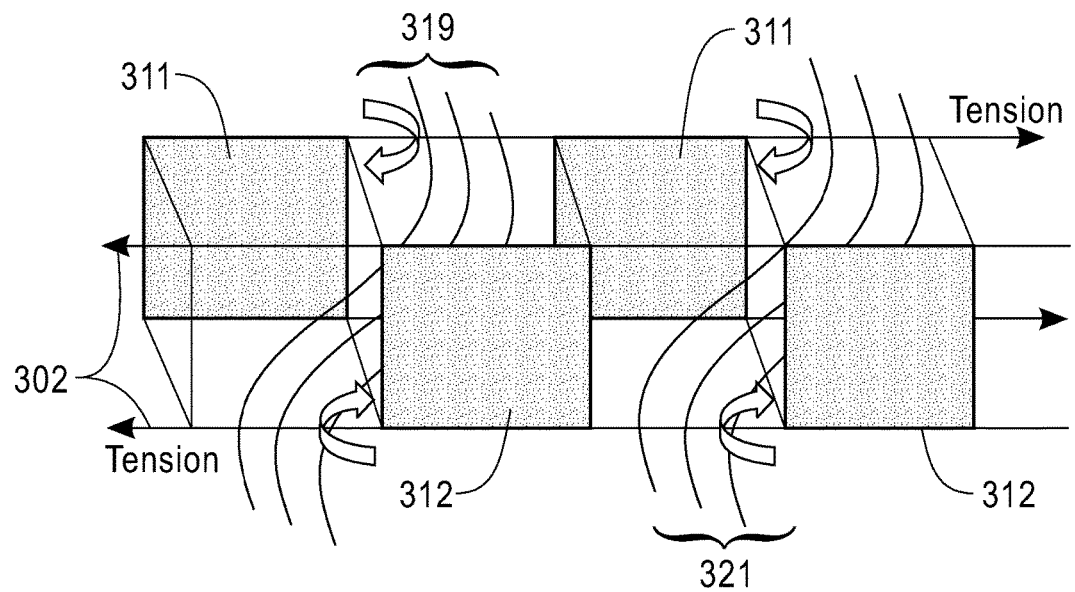
FIG. 4 shows still another exemplary implementation according to an embodiment of the present invention.

Referring to FIG. 4, shown is another active plane control of threads according to another embodiment of the present invention. Plane areas 311 and 312 of the clothing includes a plurality of threads having tension points 302. When the tension points 302 are pulled in a certain direction air flow (319, 321) can be either increased or decreased. For example, as horizontal threads in each layer tightens, the layers separate and allow for a path for ventilation. If the horizontal threads are allowed to returned to a normal position, the air flow is decreased and creates loft.

The embodiments of the present invention uses active monitoring and control to provide better technical clothing to provide for:
 Variable insulation clothing
 Variable breathability clothing, and
 Monitoring used to control the insulation of the clothing
  Examples:
   Increased respiration and pulse, combined with increasing body temperature→lower the insulation of the clothes Sudden decrease in movement (stopping for a break)→increase insulation of the clothes.

The embodiments of the present invention provide for controlling the insulation of the active technical clothing by changing the loft. The loft may be temperature driven controlled regarding the deformation of the material. The actively controlled deformation may use either electrical or optical control signals. Some materials used in the clothing may use shape memory polymers which are controlled by light or electrical signals.

The embodiments of the present invention provide for comfort control by controlling the shape of the clothing through heating management and predictions.

Figure 5:
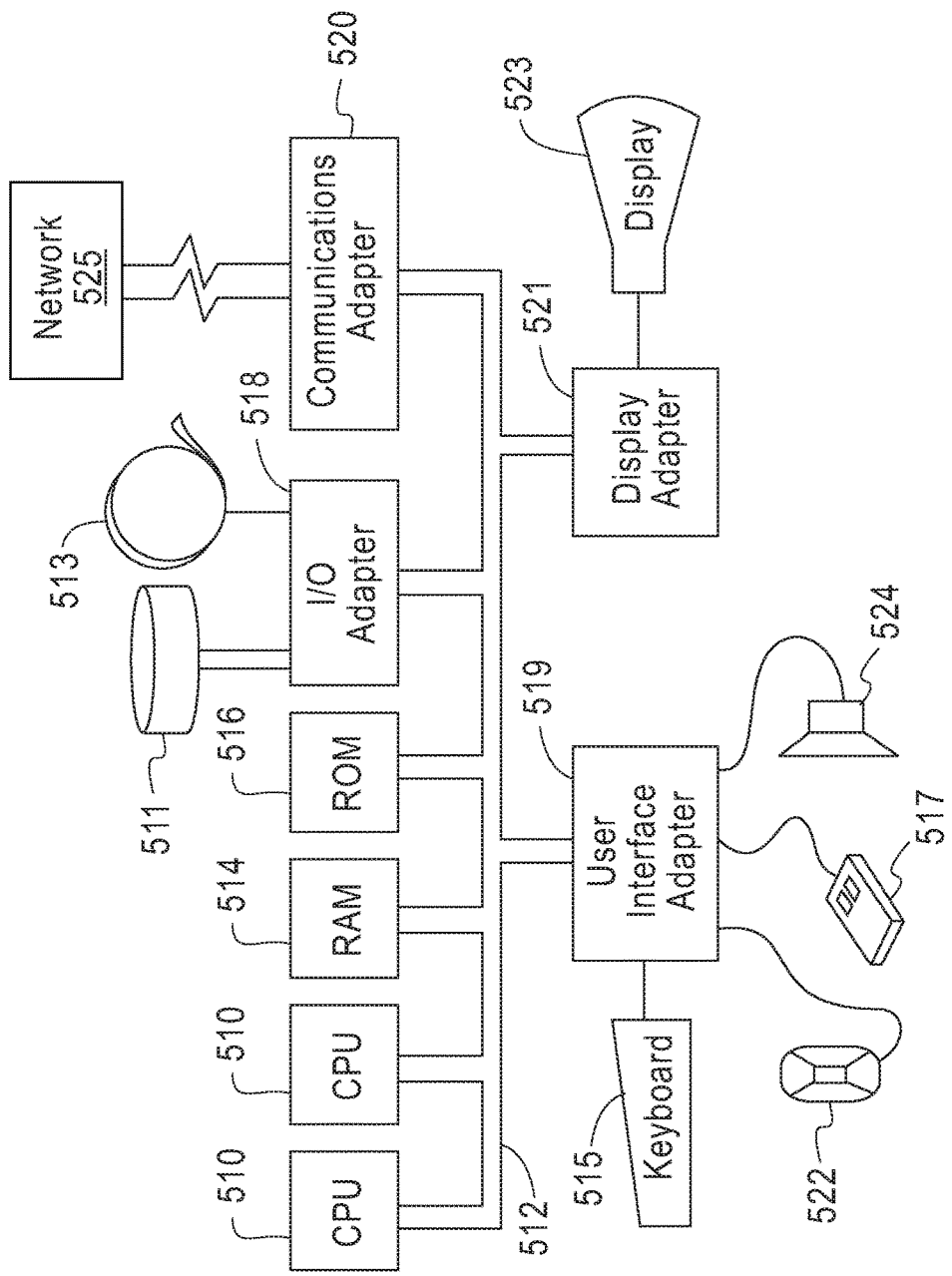
FIG. 5 illustrates a hardware configuration according to an embodiment of the present invention.

Referring now to FIG. 5, this schematic drawing illustrates a hardware configuration of an information handling/ computer imaging system in accordance with the embodiments of the invention. The system comprises at least one processor or central processing unit (CPU) 510. The CPUs 510 are interconnected via system bus 512 to various devices such as a random access memory (RAM) 514, read-only memory (ROM) 516, and an input/output (I/O) adapter 518. The I/O adapter 518 can connect to peripheral devices, such as disk units 511 and tape drives 513, or other program storage devices that are readable by the system. The system can read the inventive instructions on the program storage devices and follow these instructions to execute the methodology of the embodiments of the invention. The system further includes a user interface adapter 519 that connects a keyboard 515, mouse 517, speaker 524, microphone 522, and/or other user interface devices such as a touch screen device (not shown) to the bus 512 to gather user input. Additionally, a communication adapter 520 connects the bus 512 to a data processing network 525, and a display adapter 521 connects the bus 512 to a display device 523 which may be embodied as an output device such as a monitor, printer, or transmitter, for example.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising: embedding clothing with at least one sensor and at least one control unit; a power unit powering on the at least one sensor and the at least one control unit;
   the at least one sensor monitoring a sensed condition; the at least one control unit conducting a heat prediction based on the sensed condition; and
   the at least one control unit controlling threads within the clothing based on the heat prediction to actively adjust properties of the clothing;
   wherein the actively adjusted properties include changing fabric deformation of the clothing;
   wherein the changing of the fabric deformation is achieved by adjusting the tension of the threads of the clothing for allowing a change of airflow within the clothing.

2. The method according to claim 1, wherein the actively adjusted properties include changing breathability of the clothing.

3. The method according to claim 1, wherein the actively adjusted properties include changing insulation ability of the clothing.

4. The method according to claim 1, wherein the changing of the fabric deformation increases loft.

5. The method according to claim 1, wherein the changing of the fabric deformation creates a series of offset openings through which the air can flow through.

\* \* \* \* \*